United States Patent [19]

Vestergaard et al.

[11] 4,196,385

[45] Apr. 1, 1980

[54] METHOD AND APPARATUS FOR MEASURING THE CONCENTRATION OF FLUIDS

[75] Inventors: Peter Vestergaard, Holeby; Günther Møller; Rud F. Madsen, both of Nakskov, all of Denmark

[73] Assignee: Aktieselskabet de Danske Sukkerfabrikken, Copenhagen, Denmark

[21] Appl. No.: 864,799

[22] Filed: Dec. 27, 1977

[30] Foreign Application Priority Data

Dec. 30, 1976 [DK] Denmark ............................. 5901/76

[51] Int. Cl.² ...................... G01F 23/28; G01R 27/04; C13F 1/02
[52] U.S. Cl. ............................ 324/58.5 B; 23/230 A; 127/16; 127/61
[58] Field of Search .............. 324/58.5 B, 58 B, 58 R; 127/15, 16, 61, 62; 23/230 A

[56] References Cited

U.S. PATENT DOCUMENTS

| | | | |
|---|---|---|---|
| 3,424,002 | 1/1969 | Johnson | 324/58.5 B |
| 3,474,337 | 10/1969 | Petrick | 324/58.5 B |
| 3,572,119 | 3/1971 | Bak | 324/58.5 B X |
| 3,695,107 | 10/1972 | Hertz et al. | 324/58.5 B |
| 3,703,829 | 11/1972 | Dougherty | 324/58.5 B |
| 3,812,422 | 5/1974 | DeCarolis | 324/58.5 B |
| 3,832,900 | 9/1974 | Ross | 324/58.5 B X |
| 3,853,005 | 12/1974 | Schendel | 324/58.5 B X |
| 3,995,212 | 11/1976 | Ross | 324/58.5 B |
| 4,054,255 | 10/1977 | Magenheim | 324/58.5 B X |

*Primary Examiner*—Rudoloph V. Rolinec
*Assistant Examiner*—Ernest F. Karlsen
*Attorney, Agent, or Firm*—Watson, Cole, Grindle & Watson

[57] ABSTRACT

In a method and apparatus for measuring the concentration of a fluid depending on the dielectric constant of the fluid, electric oscillations are supplied from a source through an impedance matching link to an antenna placed in the liquid within the confines of a Faraday cage, and the electric power reflected from the antenna towards the source is measured to determine deviations from ideal matching resulting from changes of the dielectric constant of the fluid. In an important embodiment, the measurement is used for the automatic programmed control of the supply of syrup in a sugar crystallization process in accordance with a predetermined program.

2 Claims, 1 Drawing Figure

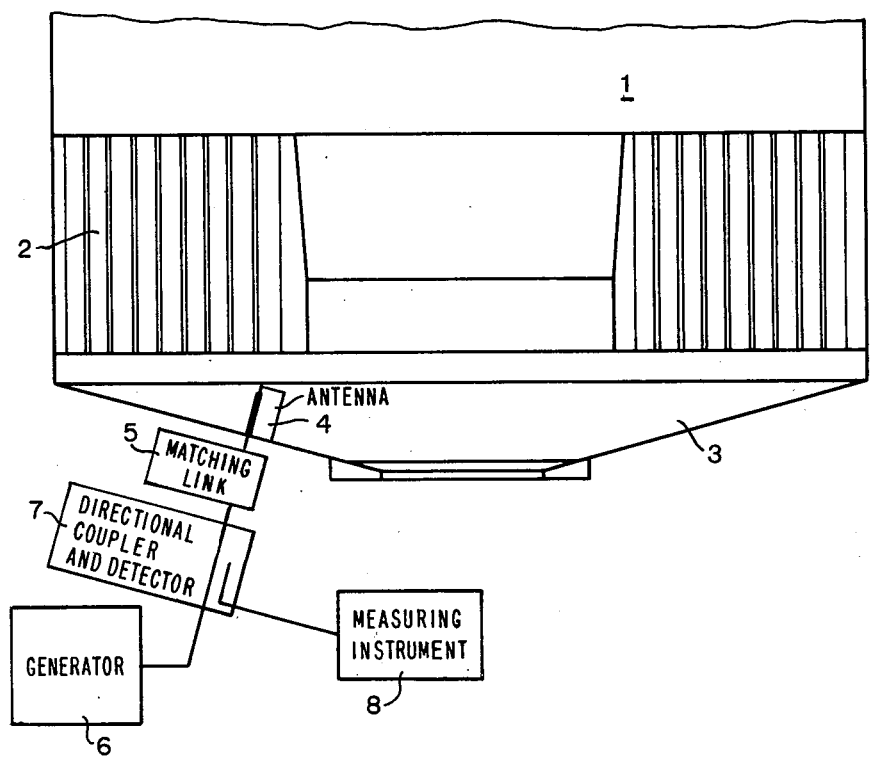

METHOD AND APPARATUS FOR MEASURING THE CONCENTRATION OF FLUIDS

BACKGROUND OF THE INVENTION

The invention relates to a method and apparatus for measuring the concentration of fluids such as liquids, emulsions, suspensions or slurries, particularly fluids containing water as a substantial component.

Within many industries it is desirable during the processing of a fluid to continuously monitor and control the concentration of the fluid. Under present day practices such continuous watching and control is frequently based on various indirect measurements such as measurement of density, refractive index, increase of boiling point, electric conductivity, viscosity, absorbtion of light or absorbtion of radioactive radiation. Each of these measuring methods has its advantages and its limitations.

Thus, in connection with vacuum pans for the crystallization of sugar, an important example of the processes with which the invention is concerned, the following measuring methods have been used in practice for measuring the concentration required for the crystallization condition:

(1) Electric conductivity: This measuring method has been found practical and satisfactory for products with a salt content above ½% of total dry matter, if this salt content does not vary substantially with time. The measurement is based on the conductivity of the syrup enclosing the crystals, but is also to some extent influenced by the crystal percentage in the crystal-fluid mixture. This dependence has in practice been found very satisfactory for the purpose mentioned. However, the measuring method fails at low and varying contents of salt.

(2) Increase of boiling point and refractive index: This measurement depends exclusively on the concentration of the mother syrup.

Seeing that towards the end of a crystallization where the mother syrup constitutes a saturated or only slightly supersaturated sugar solution, the concentration of which practically does not change, it is necessary to employ a measuring method which also depends on the crystal percentage; thus this measuring methods cannot be used in the conduction of the whole crystallization process.

(3) Measurement of viscosity or consistency: This measuring method is today successfully used for controlling the crystallization process. The equipment required for the measurement is, however, relatively complicated and the measuring method is somewhat more dependent on crystal percentage than desirable.

The other measuring methods mentioned above are normally not used for the crystallization process on account of practical difficulties.

It is known that the dielectric constant of many fluids varies with the concentration of the fluid and that the impedance of an antenna immersed in a fluid depends on the dielectric constant of the fluid. These facts have been utilized in various methods for measuring the water content of fluids. Thus, the U.S. Pat. No. 3,612,996 discloses a method of measurement depending on microwave resonance in a fluid-filled cavity specially constructed for the purpose, and the U.S. Pat. No. 3,684,952 discloses a method depending on the change of resonance frequency of an oscillator caused by an antenna immersed in a fluid.

SUMMARY OF THE INVENTION

It is an object of the invention to provide a measuring method and apparatus which are likewise based on the dielectric constant of a fluid and its influence on the impedance of an antenna but which do not depend on resonance phenomena and are therefore easier to install for many uses, particularly in connection with standard equipment for the processing of liquids, the concentration of which is to be monitored and controlled during such processing.

It is a further object of the invention to provide a measuring method and apparatus which are particularly suitable for monitoring and controlling the concentration of the sugar fluid in vacuum pans for the crystallization of sugar during the progress of crystallization.

According to the present invention, a method of measuring the concentration of a fluid, the dielectric constant of which depends on concentration, is characterized in that electric oscillation of constant power and constant frequency are supplied from a source of such oscillations to an antenna mounted in a container for the liquid and within the confines of a Faraday cage formed in the container and filled with fluid, and the power of the signal reflected from the antenna in the case of deviation from ideal matching of the impedances of the antenna and the source is measured, the electric oscillations having a frequency so high that the electric conductivity has no substantial influence on the result of the measurement.

As will be observed this method does not depend on any resonance phenomena, but instead on a measurement of the matching of impedances. Moreover, due to the placing of the antenna within the confines of a Faraday cage filled with fluid, the actual propagation of waves in the fluid is of little avail and the mechanical dimensions of the processing apparatus therefore have little influence on the measurement. The adaptation of the measuring apparatus to any standard fluid processing apparatuses is therefore a simple matter.

Moreover, it has been found that when the measuring method and apparatus according to the invention are used for monitoring and controlling the concentration in a vacuum pan for the crystallization of sugar, the concentration value determined by the method strikes a suitable balance between the concentration of the syrup and the crystal percentage so that the measuring method can be used during the whole progress of the crystallization process right up to the termination of this process.

BRIEF DESCRIPTION OF THE DRAWING

The single FIGURE of the drawing shows diagrammatically a measuring apparatus according to a preferred embodiment of the invention as mounted on a vacuum pan for use in the crystallization of sugar.

DESCRIPTION OF THE PREFERRED EMBODIMENT

In the drawing, 1 is a vacuum pan for the crystallization of sugar, the lower portion of the outer wall of the vacuum pan having been broken away to show the usual pipe heating system 2 and the bottom chamber 3 of the vacuum pan.

In the bottom of the vacuum pan 1 there is mounted a rod antenna 4, which via an adjustable impedance matching link or impedance transformer 5 is connected to a VHF-generator 6, which serves as a source of electric oscillations of constant power and constant frequency within the VHF-range.

In the supply conductor from the generator 6 to the antenna 4 there is provided a directional coupler 7 with a built-in detector connected to a measuring instrument 8, such as a voltmeter. The antenna C may be a simple rod antenna which is very resistant to the rather violent flow of fluid that may occur in its surroundings.

As is well known in the field of electric circuitry, the maximum electric power will be absorbed in a load when the impedance of the load, as seen from the generator, is equal to the impedance of the generator or in other words when the two impedances are matched.

The same applies to radiation of electric power from an antenna, the maximum possible electric power being supplied to the antenna for radiation when the impedances of the antenna and the generator are matched.

Since the impedance depends on the configuration and surroundings of the antenna, it is necessary to provide an impedance transformation between the antenna used in a particular case and a generator in order to obtain the maximum possible supply of electric power to the antenna. This impedance transformation is well known in the electric circuitry art.

The form of an impedance transformation or impedance matching is different depending on the frequency used as is well known in electric filter technique.

If an impedance matching is not obtained, part of the electric power supplied by the generator will be reflected by the load towards the generator. This is expressed by the formula $$Pr = P_G \cdot \frac{|Z_G - Z_B|}{Z_G + Z_B}$$

where
$P_G$=the electric power emitted by the generator,
$Pr$=the electric power reflected by the load,
$Z_G$=the impedance of the generator,
$Z_B$=the impedance of the load.

From the above equation it will be seen that the reflected effect $Pr=0$ for $Z_G=Z_B$ and that a change of $Z_B$ will result in a change of $Pr$.

In the extreme situations it will be seen that $Pr=P_G$ if $Z_B=0$ (short-circuiting) or $Z_B=\infty$ (open circuit).

Since the impedance of any particular antenna depends on its surroundings and on the dielectric constant of the surrounding medium, it will be seen that a change of the dielectric constant of the surrounding medium will result in a change of the reflected electric power. By effecting an optimum matching at a constant frequency, it can now be obtained that the value $Z_G$-$Z_B$ is practically 0 at a certain dielectric constant of the surrounding medium and thereafter any change of the dielectric constant will make the value $Z_G$-$Z_B$ different from 0.

From the literature it is known that the dielectric constant $\epsilon$ of a composite medium can be expressed as an additive function of the dielectric constants $\epsilon_1$, $\epsilon_2$, etc. of the components of the medium as follows:

$$\epsilon = \epsilon_1 \cdot \phi_1 + \epsilon_2 \cdot \phi_2,$$

where $\phi_1$ and $\phi_2$ are the volume concentration of the components which is the basis of the measuring principle. Thus, in the fluid present in a sugar crystallization vacuum pan, the measured value of the dielectric constant will be an additive function of the dielectric constants of water, dissolved sugar and crystallized sugar.

The measurement can preferably be performed in one of the following manners:

(1) The matching link 5 is adjusted for a minimum of return electric power from the antenna 4 at a given concentration. In practice, this will not be exactly 0, but as mentioned above practically equal to 0. Any change of the concentration or crystallization state of the fluid will now result in a change of the impedance of the antenna which can be read out by means of the measuring instrument 8.

It is observed that the constancy of the electric power emitted by the generator 6 is not over-critical. To eliminate the effect of minor variations of the said electric power emitted by the generator 6, the electric power measured by the instrument 8 may, if desired, be put in relation to the electric power of 6 so as to express the measurement in percentage of the emitted power.

(2) During continuous measurement, the impedance matching link 5 is continuously adjusted for minimum of return electric power from the antenna 4, and the position of adjustment of the matching link 5 during the progress of the crystallization is used as an expression of the concentration and thereby the crystallization state.

In this case the effect of minor changes of the electric power emitted by the generator 6 will automatically be eliminated.

The constancy of frequency of the generator 6 is not over-critical either, the main point being that changes of the impedance of the antenna 4 should not appreciably affect the said frequency. For the correct functioning of the measuring, it is necessary that the antenna is placed so that the surrounding walls constitute an efficient and uniform Faraday cage which should be filled with fluid. This condition is fulfilled by placing the antenna 4 at the bottom of a vacuum pan as illustrated where the metallic surface of the pipe heating system present above the antenna effects the necessary screening also against varying level of the fluid (massequite).

For the measurement, any frequency in the VHF-range may on principle be used. The higher the frequency, the more the measurement will become independent of the salt content of the fluid. The preferred frequency range is between about 30 MHz and about 1 GHz.

In carrying out a batch-wise crystallization of sugar in a vacuum pan, a predetermined quantity of undersaturated syrup is first supplied to the pan and is evaporated by boiling under vacuum to a point of slight supersaturation. Then a predetermined quantity of seeding material, e.g. in the form of sugar dust or sugar dust suspension, is added and as crystallization proceeds, additional syrup is supplied to the pan. The additional supply of syrup is controlled during the whole progress of crystallization in such a manner as to obtain at any time during the crystallization a concentration which varies slowly in accordance with a program determined once and for all by experiment and experience. It has been found that once this program has been established for a particular apparatus as used for a particular process, the measuring method according to the invention can be used for the automatic control in accordance with such a program by well known methods of programmed control governed by the concentration value read out on the instrument 8.

If found necessary, the measurement can be temperature compensated.

We claim:

1. A method for the programmed control of the supply of syrup in a batchwise sugar crystallization process taking place in a vacuum pan having a pipe heating system and a bottom chamber forming a Faraday cage filled with fluid, the method comprising supplying electric oscillations of constant power and constant frequency from a source of such oscillations through an adjustable impedance matching link to an antenna mounted in said bottom chamber in direct contact with the fluid therein during the progress of the crystallization in the pan, adjusting said matching link for minimum reflection from the interface of the antenna and the fluid in the pan at a given concentration of the fluid, and during the progress of crystallization, measuring the power of the signal reflected from the interface of the antenna and the fluid in the pan as a consequence of deviation from ideal matching of the impedances of the antenna and the source, and using the measurement as an input signal for the programmed control of the supply of syrup in accordance with a predetermined program, the electric oscillations having a sufficiently high frequency such that the electric conductivity has no substantial influence on the result of the measurement.

2. A method for the programmed control of the supply of syrup in a batchwise sugar crystallization process taking place in a vacuum pan having a pipe heating system and a bottom chamber forming a Faraday cage filled with fluid, comprising supplying electric oscillations of contant power and constant frequency from a source of such oscillations through an adjustable impedance matching link to an antenna mounted in said bottom chamber in direct contact with the fluid therein during the progress of the crystallization in the pan, continuously adjusting said matching link for minimum reflection from the interface of the antenna and the fluid in the pan during the progress of crystallization, and using the position of adjustment of the matching link as an input signal for the programmed control of the supply of syrup in accordance with a predetermined program, the electric oscillations having a sufficiently high frequency such that the electric conductivity has no substantial influence on the result of the measurement.

* * * * *